United States Patent [19]
Kershaw et al.

[11] Patent Number: 5,986,164
[45] Date of Patent: Nov. 16, 1999

[54] ALGINATE WOUND DRESSINGS

[75] Inventors: David Kershaw; Peter Michael John Mahoney, both of Clwyd, United Kingdom

[73] Assignee: Bristol-Myers Squibb Company, New York, N.Y.

[21] Appl. No.: 08/619,740

[22] PCT Filed: Sep. 16, 1994

[86] PCT No.: PCT/GB94/02024

§ 371 Date: May 16, 1996

§ 102(e) Date: May 16, 1996

[87] PCT Pub. No.: WO95/09658

PCT Pub. Date: Apr. 13, 1995

[30] Foreign Application Priority Data

Oct. 1, 1993 [GB] United Kingdom .................. 9320232

[51] Int. Cl.$^6$ .............................. A61F 13/00; A61F 15/00
[52] U.S. Cl. ................................ 602/49; 602/52; 424/447
[58] Field of Search .................................. 602/41, 48, 49, 602/52, 58; 424/445, 447, 449; 514/54, 62

[56] References Cited

U.S. PATENT DOCUMENTS

| | | | |
|---|---|---|---|
| 5,238,685 | 8/1993 | Wren | 424/445 |
| 5,482,931 | 1/1996 | Thompson | 424/445 |

FOREIGN PATENT DOCUMENTS 9316111  8/1993  Germany ........................ A61K 49/00

*Primary Examiner*—Wynn Wood Coggins
*Assistant Examiner*—Jennifer R. Sadula
*Attorney, Agent, or Firm*—John M. Kilcoyne; Theodore R. Furman, Jr.

[57] ABSTRACT

A wound dressing which comprises alginate characterized in that the alginate has a mannuronate content of 50% to 80% has a molecular weight of 7,000 to 40,000 and has a monovalent:polyvalent of from 10 to 30:70 to 90.

10 Claims, No Drawings

ALGINATE WOUND DRESSINGS

The present invention relates to wound dressings, components thereof and to the methods of their manufacture. More specifically this invention relates to dressings suitable for use on exuding wounds, to alginate fibres for use therein and to the methods of their manufacture.

Exuding wounds such as ulcers, pressure sores and burns tend to produce copious volumes of exudate through at least part of the healing process. Many methods of coping with highly exuding wounds have been suggested, for example covering the wound with a highly permeable adhesive film, covering the wound with an adhesive hydrocolloid dressing or employing a dressing comprising an alginate. The use of an alginate wound dressing has proved to have many advantages, for example in terms of aiding healing of the wound as avoidance of damaging friable tissue on removal. Such dressings are described in: PCT/GB89/00706, EP 89917135.6, EP 89910126.5, EP 9120236.4 and PCT/GB92/00792.

Although known alginate dressings have good solubilities, there can be difficulties in removing them from wounds, for example in use they can partially dissolve to a weak gel which has to be washed from the wound. A more soluble dressing would be desirable to ease the removal by washing. Such a dressing has now been discovered.

In addition, it is known that alginate dressings have considerable disadvantages in that they, in common with other forms of dressing, do not sufficiently prevent tissues surrounding highly exuding wounds from becoming macerated. Maceration is not desirable because it can lead to increased friability of tissue. There is therefore a desire to provide a flat alginate dressing which is less likely to allow maceration of tissue surrounding highly exuding wounds. Such a flat dressing has now been discovered.

The present invention provides a wound dressing which comprises alginate characterised in that the alginate has a mannuronate content of 50% to 80%, has a molecular weight of 7000 to 40000 and has a monovalent:polyvalent ion content of from 10 to 30:70 to 90.

It has been found that dressings of the invention and the fibres of which they are composed hydrate rapidly. This greatly helps removal of the dressings and, in the case of flat dressings, significantly reduces the amount of lateral transport of fluid by capilarity. This in turn reduces the amount of exudate transported to the tissue surrounding the exuding wound so that the tendency for that tissue to become macerated is reduced or eliminated.

Alginates are produced by a variety of micro-organisms and marine algae which are the normal commercial source. The alginates being natural materials show considerable variety but are characterised in being block copolymers, the individual monosaccharide units being arranged into groups as blocks of mannuronic (M) and guluronic (G) residues. In addition to the repeating blocks each polymer chain can contain a proportion of alternating M and G monosaccharide units. It has been found that alginates containing 50% to 80% mannuronate can (if having an appropriate molecular weight and ionic content) be of particular use in wound dressings.

Alginates containing 50% to 85% of mannuronate can be obtained from species such as *Ascophyllum nodosum, Durvillea Protatonum, Lasonia Nigrescens* and *Ecklonia Maxima*. Blends may be used if desired. Favoured alginates for use in the dressings of this invention will contain from 60% to 80% and preferably from 70% to 75% of mannuronate. A suitable source of such materials is Kelco, Tadworth, Surrey, UK. Suitable grades include manacol of the appropriate molecular weight range.

It has been found that the desirable properties of the dressings are best achieved if the molecular weight of the alginate is from 5000 to 80000, aptly from 7000 to 40000, more suitably from 12000 to 35000 and preferably from 15000 to 30000, for example about 20000 to 25000. A fairly broad distribution of molecular weights within the alginate polymer population is acceptable. The molecular weight referred to is the number average molecular weight. One suitable method of determining the number average molecular weight is given in the descriptions hereinafter. (Thus the molecular weight is aptly at least 5000, more aptly at least 7000, yet more aptly at least 15000 and favourably, is at least 20000 aptly less than 80000, more aptly less than 40000, yet more aptly less than 35000 and more suitably less than 30000.

It has also been found that the desirable properties of the dressings are best achieved if the ratio between polyvalent ions (normally divalent ions) such as calcium and monovalent ions such as sodium is from 70–90:30–10, more suitably from 75–85:25–15 and preferably 80:20. Obviously small amounts of other ions may be present as long as they are pharmaceutically acceptable and do not interfere with the properties of the dressing.

A particularly suitable dressing of this invention will comprise alginate characterised in that the alginate has a mannuronate content of 60% to 80%, a molecular weight of 15000 to 25000 and a ratio of sodium ion to calcium ions of 15 to 25:75 to 85.

A preferred dressing of this invention will comprise alginate characterised in that the alginate has a mannuronate content of 70% to 75%, a molecular weight of about 20000 and a ratio of calcium ion to sodium ion 80:20.

The alginate is normally and preferably present as fibres. The fibres may be long or short, tangled or untangled, knitted or woven as desired. The dressing may be in the form of a flat needled or non-needled wound dressing, a sliver product (which is particularly suitable for cavities), a roving product (which is especially suitable for use in sinus cavities), an island dressing, as a yarn or knitted or woven fabric. The previously described patent applications (which are incorporated herein by reference) may be inspected for suitable dressing formats and manufacturing methods etc.

A wound dressing according to the present invention may further be provided with a moisture vapour permeable film, for example a polyurethane, polyetherester derivatives, a polyether amide and the like. Generally the polymers will be hydrophilic. Aptly such films will be from 15 to 50 microns thick, more usually 20 to 30 microns, for example 25 microns. The film layer may be applied directly to the surface of an alginate pad but more suitably will be adhered by means of an adhesive. Such adhesives are preferably moisture vapour permeable, for example an acrylic, polyurethane or polyether adhesive of which acrylic adhesives are preferred.

Dressings of this invention are normally provided sterile contained within a bacteria proof pouch.

A particularly suitable dressing of this invention comprises a pad of alginate fibres. These pads can be referred to as a "flat" dressing because they are generally produced flat but of course they can be flexible and adapt to the shape of a wound. In general these are provided as pads of from 4×4×0.1 cm up to 20×20×0.3 cm although other shapes and sizes are common. Dressings of this type are generally laid over exuding wounds such as ulcers or burns. The dressings of this invention do not need to be cut to shape to avoid maceration when used in this manner. They are particularly easy to remove because even if the wound covering portion gels or dissolves, the integrity of the wound surrounding portion is maintained and so allows the dressing to be lifted off. If any residual material is left in the wound it is particularly easy to remove by irrigation because of the high solubility of the fibres.

When used to cover exuding wounds and even when over-wrapped with four layers of compression bandage, dressings of this invention were found not to cause maceration of surrounding skin and to be easily removed.

The dressings of this invention may be made in conventional manner, for example as described in the previously mentioned patents. They may contain antioxidants or preservatives if desired. The dressings may be sterilized by radiation if desired.

Description 1

A suitable method of molecular weight determination of alginate wound dressings.

Alginate solutions were prepared from wound dressing samples by titration with a concentrated aqueous Calgon solution (that is sodium hexametaphosphate, for example at 10% w/w). The Calgon solution was added dropwise to the wound dressing fibres, which were agitated with a magnetic stirring bar until the fibres had dissolved and a non-turbid solution was obtained. The concentrated (approximately 0.7%) alginate solutions were diluted with aqueous sodium nitrate to yield solutions containing approximately 0.2% alginate and 0.1M $NaNO_3$. The dilute alginate solutions were filtered through a 0.45 micron filter prior to injection into the Size Exclusion chromatography/Multiple Angle Laser Light Scattering instrument (SEC/MALLS).

Molecular weight distributions were determined by SEC/MALLS. Our suitable system comprises a Hewlett-Packard Liquid Chromatograph Model 1084B, a 30 cm Ultrahydrogel Linear column (Waters) with a guard column, a DAWN Model F Light Scattering Detector and a Waters 410 Differential Refractometer. The sample is injected into the eluant flow (aqueous 0.1M $NaNO_3$ with 0.01% $NaN_3$ as an antimicrobial agent) and is separated based on molecular size by the size exclusion chromatography column. As the sample elutes from the column the molecular weight and concentration profiles are determined by the light scattering and refractive index detectors, respectively. An index of refraction increment (dn/dc) of 0.145 was used to determine the sample concentration (and molecular weight) as a function of elution volume. This value was obtained from the literature (Paoletti et al (1991) Carbohydrate Polymers, 15, 171; Mackie et al (1980) Biopolymers J 19, 1839; Strand et al (1982) Macromolecules, 15, 570) and is typical for alginates in aqueous salt solutions. The light scattering detector was calibrated with a series of pullulan standards (Mw=200,000; 400,000 and 800,000 g/mole) and a previously measured (by Paoletti) alginate sample of Mw=210,000.

Weight average and number-average molecular weights, as well as polydispersity indices (Mw/Mn), were determined for each sample. The molecular weight results for the algin samples are given in the table below.

| Sample | Mn*(g/mole) | Mw(g/mole) | Mw/Mn |
|---|---|---|---|
| Example 1 | 21,000 | 92,000 | 4.4 |
| SORBSAN | 120,000 | 300,000 | 2.5 |

The SORBSAN wound dressing has much higher and significantly different molecular weight distribution than the sample of Example 1 (Mw=300,000 vs. 92,000 g/mole). Example 1 had a broader molecular weight distribution than that of SORBSAN.

EXAMPLE 1

Manufacture of Low Molecular Weight, High Mannuronate, 80:20 Alginate Fabric (a) Low Molecular Weight, High Mannuronate Calcium Alginate Fibre The fibre was prepared by the method of preparation 1 of PCT/GB89/01009 employing sodium alginate powder wherein the alginate had a number average weight molecular weight of 21,000 and had a mannuronate content of 70%.

(b) Low Molecular Weight, High Mannuronate, 80:20 Alginate Fabric Manufacture of The fabric was prepared by the method of preparation 2 of PCT/GB89/01009 but employing low molecular weight, high mannuronate calcium alginate fibre as prepared in part (a).

EXAMPLES 2–5

Alternative Manufacture of Low Molecular Weight, High Mannuronate, 80:20 Alginate Fabric.

The fabrics were prepared by the methods of preparations 3 to 6 of PCT/GB98/01009 adapted by the use of calcium alginate as prepared in Example 1(a) herein.

EXAMPLES 6

A fabric as prepared in Example 1 was cut to 5 cm×5 cm square and placed in the centre of a water vapour permeable polyurethane film of 8 cm×8 cm square and 21 microns thick. The face of the film on which the fabric was placed was provided with a pressure sensitive adhesive layer comprising an acrylic adhesive. A silicone release paper was then placed on the remote face of the film and the paper was trimmed to size.

We claim:

1. A wound dressing which comprises alginate wherein the alginate has a unit mannuronate content of 50% to 80%, has a number average molecular weight of 7000 to 40000 and has an equivalent ratio of monovalent:polyvalent ion of 10 to 30:70 to 90.

2. A dressing according to claim 1, which has a unit mannuronate content of 60 to 80%.

3. A dressing according to claim 2, which has a unit mannuronate content of 70 to 75%.

4. A dressing according to claim 1, wherein the alginate has a number average molecular weight of 12000 to 35000.

5. A dressing according to claim 4, wherein the alginate has a number average molecular weight of 15000 to 30000.

6. A dressing according to claim 1, which has an equivalent ratio of monovalent:polyvalent ion of 15 to 25:75 to 85.

7. A dressing according to claim 1, wherein the monovalent ion is sodium and the polyvalent ion is calcium.

8. A wound dressing which comprises alginate wherein the alginate has a unit mannuronate content of 60% to 80%, a number average molecular weight of 15000 to 25000 and an equivalent ratio of sodium ion to calcium ion of 15 to 25:75 to 85.

9. A wound dressing which comprises alginate wherein the alginate has a unit mannuronate content of 70% to 75%, a number average molecular weight of about 20000 and an equivalent ratio of calcium ion to sodium ion of 80:20.

10. A dressing according to claim 9, which further comprises a moisture vapour permeable film.

* * * * *